US012797589B2

(12) United States Patent
Ikoma

(10) Patent No.: US 12,797,589 B2
(45) Date of Patent: Nov. 17, 2026

(54) BALLOON FOR BALLOON CATHETER, BALLOON CATHETER, AND METHOD FOR MANUFACTURING BALLOON CATHETER

(71) Applicant: KANEKA CORPORATION, Osaka (JP)

(72) Inventor: Kazuaki Ikoma, Osaka (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 19/205,179

(22) Filed: May 12, 2025

(65) Prior Publication Data

US 2025/0269152 A1 Aug. 28, 2025

Related U.S. Application Data

(63) Continuation of application No. PCT/JP2023/036993, filed on Oct. 12, 2023.

(30) Foreign Application Priority Data

Nov. 16, 2022 (JP) ................................ 2022-183695

(51) Int. Cl.
*A61M 25/10* (2013.01)

(52) U.S. Cl.
CPC .... *A61M 25/1002* (2013.01); *A61M 25/1027* (2013.01); *A61M 2025/1043* (2013.01);
(Continued)

(58) Field of Classification Search
CPC ........... A61B 17/320725; A61B 2017/320048; A61M 25/1002; A61M 25/104;
(Continued)

(56) References Cited

U.S. PATENT DOCUMENTS 6,120,523 A * 9/2000 Crocker .............. A61M 25/104 128/898
6,544,223 B1 * 4/2003 Kokish ................. A61L 29/146 604/103.02
(Continued)

FOREIGN PATENT DOCUMENTS

CN 114712672 A 7/2022
JP 2008529740 A 8/2008
(Continued)

OTHER PUBLICATIONS

International Search Report issued in International Application No. PCT/JP2023/036989, dated Jan. 9, 2024, with translation (5 pages).
(Continued)

*Primary Examiner* — Phong Son H Dang
(74) *Attorney, Agent, or Firm* — Osha Bergman Watanabe & Burton LLP

(57) ABSTRACT

A balloon for a balloon catheter including a straight tubular part, a proximal tapered part located proximal to the straight tubular part, a distal tapered part located distal to the straight tubular part, and a drug layer, is provided. The straight tubular part includes a balloon body and a convex strip which protrudes outwards in a radial direction on an outer surface of the balloon body. The drug layer is provided on the outer surface of the straight tubular part including a lateral surface of the convex strip. A crack is formed on a surface of the drug layer extending along a base of the convex strip.

18 Claims, 8 Drawing Sheets

(52) U.S. Cl.
CPC ................. *A61M 2025/105* (2013.01); *A61M 2025/1075* (2013.01); *A61M 2025/1086* (2013.01); *A61M 2205/0233* (2013.01); *A61M 2205/0238* (2013.01); *A61M 2207/00* (2013.01)

(58) Field of Classification Search
CPC .......... A61M 25/1027; A61M 25/1029; A61M 2025/1004; A61M 2025/1031; A61M 2025/1043; A61M 2025/105; A61M 2025/1075; A61M 2025/1086; A61M 2025/109; A61M 2205/0233; A61M 2205/0238; A61M 2207/00
See application file for complete search history.

(56) References Cited

U.S. PATENT DOCUMENTS

| | | | | |
|---|---|---|---|---|
| 7,572,245 | B2 * | 8/2009 | Herweck | A61P 5/00 604/103.02 |
| 7,648,727 | B2 * | 1/2010 | Hossainy | A61L 31/08 427/256 |
| 8,034,022 | B2 * | 10/2011 | Boatman | A61M 25/104 604/101.02 |
| 8,177,743 | B2 * | 5/2012 | Lennox | A61L 29/16 604/103.05 |
| 8,182,446 | B2 * | 5/2012 | Schaeffer | A61M 25/1027 604/101.02 |
| 8,636,811 | B2 * | 1/2014 | Melder | A61F 2/92 623/23.72 |
| 9,050,442 | B2 * | 6/2015 | Herweck | B29C 48/09 |
| 9,717,615 | B2 * | 8/2017 | Grandt | A61F 2/958 |
| 10,471,238 | B2 * | 11/2019 | Schneider | A61M 25/1029 |
| 11,166,742 | B2 * | 11/2021 | Schneider | A61B 17/22 |
| 11,812,987 | B2 * | 11/2023 | Madej | A61B 17/22 |
| 12,642,946 | B2 * | 6/2026 | Giasolli | A61M 25/104 |
| 2002/0010489 | A1 * | 1/2002 | Grayzel | A61F 2/958 606/194 |
| 2006/0182873 | A1 | 8/2006 | Klisch et al. | |
| 2006/0259005 | A1 | 11/2006 | Konstantino et al. | |
| 2009/0054837 | A1 | 2/2009 | Von Holst et al. | |
| 2009/0226502 | A1 | 9/2009 | Chen | |
| 2009/0227948 | A1 | 9/2009 | Chen et al. | |
| 2009/0227949 | A1 | 9/2009 | Knapp et al. | |
| 2009/0258049 | A1 | 10/2009 | Klein et al. | |
| 2010/0055294 | A1 | 3/2010 | Wang et al. | |
| 2011/0054396 | A1 | 3/2011 | Kangas et al. | |
| 2011/0160645 | A1 | 6/2011 | Sutermeister et al. | |
| 2011/0270226 | A1 | 11/2011 | Kocur et al. | |
| 2012/0053517 | A1 | 3/2012 | Chen et al. | |
| 2012/0116490 | A1 * | 5/2012 | Wesselmann | A61F 2/966 623/1.11 |
| 2012/0191111 | A1 * | 7/2012 | Aggerholm | A61B 17/320725 606/159 |
| 2012/0277843 | A1 * | 11/2012 | Weber | A61F 2/958 604/509 |
| 2013/0066268 | A1 | 3/2013 | Von Holst et al. | |
| 2013/0190725 | A1 | 7/2013 | Pacetti et al. | |
| 2013/0204179 | A1 | 8/2013 | Konstantino et al. | |
| 2013/0226071 | A1 | 8/2013 | Konstantino et al. | |
| 2013/0297003 | A1 * | 11/2013 | Pinchuk | A61F 2/95 623/1.12 |
| 2015/0012032 | A1 * | 1/2015 | Cox | A61M 25/1002 606/192 |
| 2017/0007805 | A1 | 1/2017 | Tsubooka | |
| 2017/0150988 | A1 | 6/2017 | Konstantino et al. | |
| 2019/0134359 | A1 * | 5/2019 | Kita | A61M 25/1029 |
| 2019/0321603 | A1 | 10/2019 | Konstantino et al. | |
| 2019/0344054 | A1 * | 11/2019 | Slattery | A61M 25/104 |
| 2022/0218960 | A1 | 7/2022 | Kojima et al. | |
| 2024/0115840 | A1 * | 4/2024 | Takagi | A61M 25/1011 |

FOREIGN PATENT DOCUMENTS

| | | | |
|---|---|---|---|
| JP | 2008539959 | A | 11/2008 |
| JP | 2009112361 | A | 5/2009 |
| JP | 2009525790 | A | 7/2009 |
| JP | 2011513004 | A | 4/2011 |
| JP | 2013502984 | A | 1/2013 |
| JP | 2013176507 | A | 9/2013 |
| JP | 2015217260 | A | 12/2015 |
| JP | 2017012678 | A | 1/2017 |
| JP | 2018153288 | A | 10/2018 |
| JP | 2021036924 | A | 3/2021 |
| WO | 2020250611 | A1 | 12/2020 |
| WO | 2021132141 | A1 | 7/2021 |
| WO | 2022158100 | A1 | 7/2022 |

OTHER PUBLICATIONS

International Search Report issued in International Application No. PCT/JP2023/036991, dated Dec. 5, 2023, with translation (5 pages).
International Search Report issued in International Application No. PCT/JP2023/036992, dated Dec. 5, 2023, with translation (5 pages).
International Search Report issued in corresponding International Application No. PCT/JP2023/036993, dated Nov. 28, 2023, with translation (5 pages).
International Search Report issued in International Application No. PCT/JP2023/036995, dated Jan. 9, 2024, with translation (7 pages).

* cited by examiner

BALLOON FOR BALLOON CATHETER, BALLOON CATHETER, AND METHOD FOR MANUFACTURING BALLOON CATHETER

TECHNICAL FIELD

One or more embodiments of the present invention relate to a balloon for a balloon catheter with a drug retained on its surface, a balloon catheter equipped with the balloon, and a method for manufacturing a balloon catheter equipped with the balloon.

BACKGROUND

It is known that various diseases can occur due to stenosis of blood vessels, which are the channels through which blood circulates in the body, and stagnation of blood circulation. In particular, stenosis of coronary arteries that supply blood to a heart can lead to serious diseases such as angina pectoris and myocardial infarction. Examples of a method for treating such stenosis of blood vessels include angioplasty (PTA, PTCA, and the like), which uses a balloon catheter to expand a stenosis site.

Balloon catheters with convex strips on the surface of the balloon are known (for example, Patent Literatures 1 to 5). By using such balloon catheters, when the balloon is inflated, the convex strip of the balloon can bite into a stenosis site, whereby effectively expanding the stenosis site. Meanwhile, in the case of angioplasty, restenosis can occur in the expanded stenosis site, and for reducing the frequency of such restenosis (restenosis rate), balloon catheters with a drug retained on the surface of the balloon are also known to (for example, Patent Literatures 4 to 7). By using such balloon catheters loaded with a drug, the drug can be transferred to the inner wall of a body cavity such as a blood vessel when the balloon is inflated at a stenosis or lesion site of the body cavity such as a blood vessel, and the occurrence of restenosis can be expected to be suppressed.

PATENT LITERATURES

Patent Literature 1:
Japanese Unexamined Laid-open Patent Application Publication No. 2009-112361

Patent Literature 2:
Japanese Unexamined Laid-open Patent Application Publication No. 2017-12678

Patent Literature 3:
International Patent Publication No. 2020/250611

Patent Literature 4:
Japanese Unexamined Laid-open Patent Application Publication No. 2008-539959

Patent Literature 5:
Japanese Unexamined Laid-open Patent Application Publication No. 2013-176507

Patent Literature 6:
Japanese Unexamined Laid-open Patent Application Publication No. 2008-529740

Patent Literature 7:
Japanese Unexamined Laid-open Patent Application Publication No. 2015-217260

SUMMARY

In the balloon catheter with a drug retained on the surface of the balloon, it is desirable that the drug can be efficiently transferred to the inner wall of a body cavity, such as a blood vessel wall, by expanding the balloon at a stenosis or lesion site of the body cavity such as a blood vessel. One or more embodiments of the present invention have been made in view of the above circumstance, and a balloon for a balloon catheter which can efficiently transfer a drug to a stenosis or lesion site of a body cavity such as a blood vessel, and a balloon catheter equipped with the balloon, are provided. One or more embodiments of the present invention also provide a method for manufacturing a balloon catheter equipped with the balloon of one or more embodiments of the present invention.

A balloon for a balloon catheter and a balloon catheter equipped with the balloon of one or more embodiments of the present invention, which are able to address the above, are as follows.

[1] A balloon for a balloon catheter, having a longitudinal direction extending from a proximal side to a distal side and a radial direction perpendicular to the longitudinal direction, comprising:

- a straight tubular part comprising a balloon body of a cylindrical shape and a convex strip which protrudes outwards in the radial direction on an outer surface of the balloon body;
- a proximal tapered part located proximal to the straight tubular part;
- a distal tapered part located distal to the straight tubular part; and
- a drug layer provided on the outer surface of the straight tubular part including a lateral surface of the convex strip, wherein a crack is formed on a surface of the drug layer extending along a base of the convex strip.

[2] A balloon for a balloon catheter, having a longitudinal direction extending from a proximal side to a distal side and a radial direction perpendicular to the longitudinal direction, comprising:

- a straight tubular part comprising a balloon body of a cylindrical shape and a multi-step convex strip which protrudes outwards in the radial direction on an outer surface of the balloon body;
- a proximal tapered part located proximal to the straight tubular part;
- a distal tapered part located distal to the straight tubular part; and
- a drug layer provided on the outer surface of the straight tubular part including a lateral surface of the convex strip, wherein a crack is formed on a surface of the drug layer extending along a base of any one of steps of the multi-step convex strip.

[3] The balloon according to [1] or [2] above, wherein the convex strip extends in the longitudinal direction of the balloon.

[4] The balloon according to any one of [1] to [3] above, wherein the outer surface of the straight tubular part has a convex strip-present region where the convex strip is present and a convex strip-absent region where the convex strip is not present, and a thickness of the drug layer at the base of the convex strip, excluding a part where the crack is formed, is thicker than a thickness of the drug layer at a farthest point from the convex strip in the convex strip-absent region in a cross section perpendicular to the longitudinal direction of the straight tubular part.

[5] The balloon according to any one of [1] to [4] above, wherein a drug constituting the drug layer is crystalline.

[6] The balloon according to any one of [1] to [5] above, wherein the convex strip is made of resin, metal, or a combination thereof.

[7] The balloon according to any one of [1] to [6] above, wherein the outer surface of the straight tubular part has a convex strip-present region where the convex strip is present and a convex strip-absent region where the convex strip is not present, and in a contracted state of the balloon, the straight tubular part is folded back at the convex strip-absent region with an inner surface of the balloon body facing inwards to form a folded vane portion in which the convex strip-absent regions are laminated, and the folded vane portion is disposed overlaying the outer surface of the straight tubular part and covering a top of the convex strip.

[8] The balloon according to any one of [1] to [6] above, wherein the outer surface of the straight tubular part has a convex strip-present region where the convex strip is present and a convex strip-absent region where the convex strip is not present, and in a contracted state of the balloon, the straight tubular part is folded back at the convex strip-absent region with an inner surface of the balloon body facing inwards to form a folded vane portion in which the convex strip-absent regions are laminated, and the folded vane portion is disposed overlaying the outer surface of the straight tubular part so as not to cover a top of the convex strip.

[9] A balloon catheter comprising the balloon according to any one of [1] to [8] above.

A method for manufacturing a balloon catheter of one or more embodiments of the present invention is as follows.

[10] A method for manufacturing a balloon catheter comprising the steps of:

- preparing a balloon having a longitudinal direction extending from a proximal side to a distal side and a radial direction perpendicular to the longitudinal direction, the balloon comprising a straight tubular part, a proximal tapered part located proximal to the straight tubular part, and a distal tapered part located distal to the straight tubular part, the straight tubular part comprising a balloon body of a cylindrical shape and a convex strip which protrudes outwards in the radial direction on the outer surface of the balloon body;
- applying a drug solution to the outer surface of the straight tubular part including a lateral surface of the convex strip to form a drug layer; and
- bending the convex strip relative to the outer surface of the balloon body after the step of forming the drug layer In the balloon for a balloon catheter of one or more embodiments of the present invention, a convex strip is provided on the outer surface of a straight tubular part of the balloon, a drug layer is provided on the outer surface of the straight tubular part including the lateral surface of the convex strip, and a crack extending along the base of the convex strip is formed on the surface of the drug layer. Therefore, when a balloon catheter equipped with the balloon of one or more embodiments of the present invention is used and the balloon is inflated at a stenosis or lesion site of a body cavity such as a blood vessel, the convex strip can bite into the stenosis or lesion site to effectively expand, and further, when the drug layer contacts the inner surface of the inner wall of the body cavity, the drug layer is easily peeled off from the lateral surface of the convex strip starting from the crack, and the drug layer is easily transferred from the surface of the balloon to the inner wall of the blood vessel. As a result, the drug can be efficiently transferred to the inner wall of a body cavity such as a blood vessel wall. In addition, according to the method for manufacturing a balloon catheter of one or more embodiments of the present invention, the balloon catheter can be easily manufactured.

DETAILED DESCRIPTION

Figure 1:
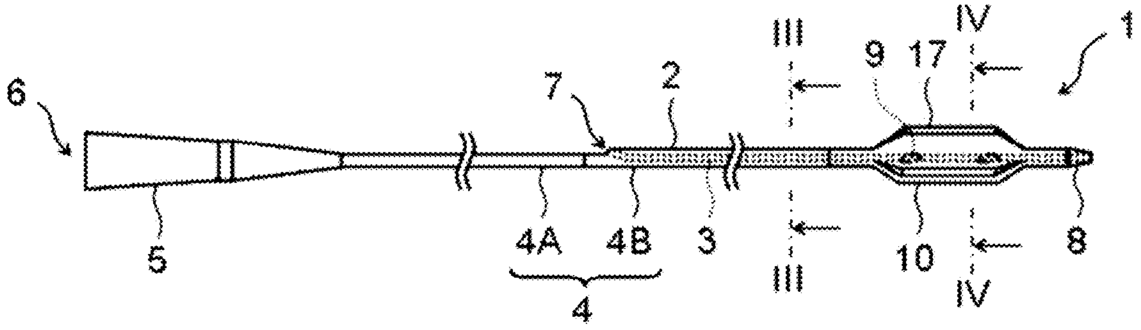
FIG. 1 shows an example of a configuration of a balloon catheter according to one or more embodiments of the present invention, and shows a lateral view of the balloon catheter without a drug layer on the surface of a balloon.

Hereinafter, one or more embodiments of the present invention are specifically explained below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of one or more embodiments of the present invention.

Figure 2:
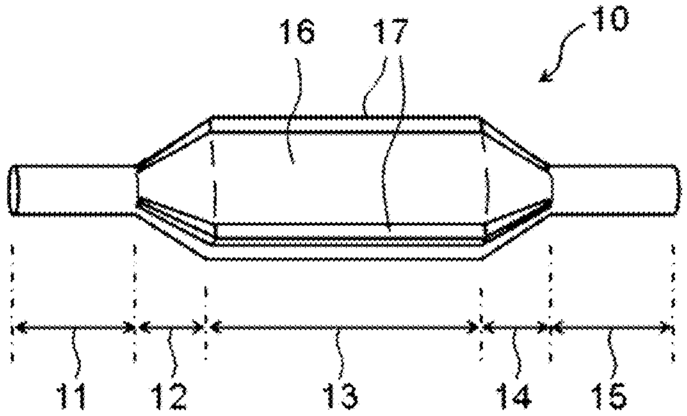
FIG. 2 shows a perspective view of a balloon provided in the balloon catheter shown in FIG. 1.
Figure 3:
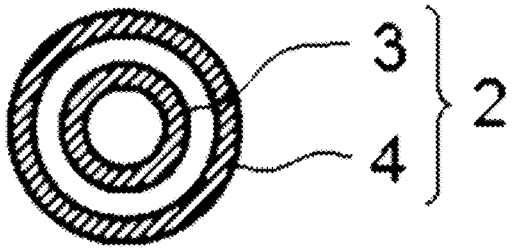
FIG. 3 shows a cross-sectional view taken along a line III-III of the balloon catheter shown in FIG. 1.
Figure 4:
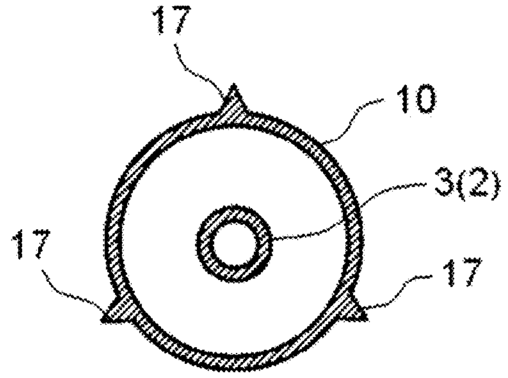
FIG. 4 shows a cross-sectional view taken along a line IV-IV of the balloon catheter shown in FIG. 1.

An example of the configuration of a balloon for a balloon catheter according to one or more embodiments of the present invention and a balloon catheter equipped with the balloon is described with reference to the drawings. FIGS. 1 to 4 show an example of the configuration of a balloon catheter without a drug layer on the balloon. FIG. 1 shows a lateral view of the balloon catheter, FIG. 2 shows a perspective view of the balloon provided in the balloon catheter shown in FIG. 1, FIG. 3 shows a cross-sectional view taken along a line III-III of the balloon catheter shown in FIG. 1, and FIG. 4 shows a cross-sectional view taken along a line IV-IV of the balloon catheter shown in FIG. 1. FIG. 1 shows an example of the configuration of a rapid-exchange type balloon catheter.

A balloon catheter 1 comprises a shaft 2 and a balloon 10 provided on an outside of the shaft 2. The balloon catheter 1 has a proximal side and a distal side, and the balloon 10 is provided in a distal part of the shaft 2. The proximal side of the balloon catheter 1 refers to a direction toward a hand of a user (an operator) with respect to a direction of extension of the balloon catheter 1, and the distal side refers to an opposite direction of the proximal side, i.e., a direction toward a treatment target side. The direction from the proximal side to the distal side of the balloon catheter 1 is referred to as a longitudinal direction.

The balloon catheter 1 is configured such that a fluid is supplied to the inside of the balloon 10 through the shaft 2, and expansion and contraction of the balloon 10 can be controlled using an indeflator (balloon pressurizer/depressurizer). The fluid may be a pressurized fluid compressed by a pump or the like. Hereinafter, the fluid supplied to the inside of the balloon 10 is referred to as a "balloon expansion fluid".

The shaft 2 is composed of, for example, an inner shaft 3 and an outer shaft 4. The inner shaft 3 is disposed in a lumen of the outer shaft 4. The inner shaft 3 can function as a guide wire insertion passage that guides an advance of the shaft 2, and when using the balloon catheter 1, a guide wire is inserted into a lumen of the inner shaft 3. The space between the inner shaft 3 and the outer shaft 4 can function as a flow path for the balloon expansion fluid.

In the rapid-exchange type balloon catheter 1, a guidewire port 7 is provided in the shaft in the middle of from the distal side to the proximal side, a proximal end of the inner shaft 3 is connected to the guidewire port 7, and a distal end of the inner shaft 3 reaches to a distal part of the shaft 2, thereby forming a guide wire insertion passage, extending from the guidewire port 7 to the distal part of the shaft 2.

The outer shaft 4 may comprise a proximal outer shaft 4A and a distal outer shaft 4B, and in this case, it may be preferable that the inner shaft 3 is disposed in the lumen of the distal outer shaft 4B. The proximal outer shaft 4A and the distal outer shaft 4B may be made of the same material, or may be made of different materials from each other. For example, it may be preferable that the proximal outer shaft 4A is made of resin or metal, and the distal outer shaft 4B is made of resin. The outer shaft 4 may not be divided into the proximal outer shaft 4A and the distal outer shaft 4B and may be composed of a single member, or the proximal outer shaft 4A and the distal outer shaft 4B may further be composed of a plurality of tube members.

It may be preferable that a hub 5 is provided on the proximal side of the shaft 2. The hub 5 may comprise a fluid injection port 6 that communicates with the flow path for the balloon expansion fluid of the shaft 2. The balloon 10, the shaft 2 (including the inner shaft 3 and the outer shaft 4), and the hub 5 can be joined using a conventional joining method such as adhesive and thermal welding.

Although not shown in the drawings, the balloon catheter may be an over-the-wire type balloon catheter in which the inner shaft extends from the distal part to the proximal part of the shaft, and a guide wire insertion passage is formed to extend from the distal side to the proximal side of the shaft. In this case, it may be preferable that the flow path for the balloon expansion fluid and the guide wire insertion passage formed in the shaft extend to the hub, and the hub is configured to comprise a fluid injection port that communicates with the flow path for the balloon expansion fluid and a treatment port that communicates with the guide wire insertion passage. It may be preferable that the hub has a bifurcated structure, and that one of the bifurcated parts is provided with the fluid injection port and the other is provided with the treatment port.

It may be preferable that coating is applied to the outer surface of the shaft 2. In the rapid-exchange type balloon catheter 1, it may be preferable that coating is applied to the outer surface of one or both of the proximal outer shaft 4A and the distal outer shaft 4B, and it may be more preferable that coating is applied to the outer surfaces of both the proximal outer shaft 4A and the distal outer shaft 4B. In the over-the-wire type balloon catheter, it may be preferable that coating is appropriated applied to the outer surface of the outer shaft.

The coating can be a hydrophilic coating or a hydrophobic coating depending on the purpose. Coating of the outer surface of the shaft 2 can be performed by immersing the shaft 2 in a hydrophilic or hydrophobic coating agent, applying a hydrophilic or hydrophobic coating agent to the outer surface of the shaft 2, or covering the outer surface of the shaft 2 with a hydrophilic or hydrophobic coating agent. The coating agent may contain a drug or an additive.

Examples of the hydrophilic coating agent include hydrophilic polymers such as polyvinyl alcohol, polyethylene glycol, polyacrylamide, such as polyvinyl polyvinylpyrrolidone and methyl vinyl ether maleic anhydride copolymer, hydrophilic coating agents made from any combination of these, and the others.

Examples of the hydrophobic coating agent include polytetrafluoroethylene (PTFE), fluorinated ethylene propylene (FEP), perfluoroalkoxyalkane (PFA), silicone oil, hydrophobic urethane resin, carbon coat, diamond coat, diamond-like carbon (DLC) coat, ceramic coat, substances terminated with alkyl groups or perfluoroalkyl groups and having low surface free energy, and others.

A distal end of the balloon catheter 1 may be provided with a tip 8. The tip 8 may be provided as a separate member from the inner shaft 3 on a distal side of the distal end of the inner shaft 3, or the inner shaft 3 may extend to a distal side of the distal end of the balloon 10, whereby the distal end part of the inner shaft 3 functions as the tip 8.

In order to enable a position of the balloon 10 to be checked under X-ray fluoroscopy, an X-ray opaque marker 9 may be provided at a part where the balloon 10 is located in the longitudinal direction. The X-ray opaque marker 9 can be provided, for example, on the inner shaft 3 located inside the balloon 10, and may be provided at positions corresponding to both ends of a straight tubular part of the balloon 10, or may be provided at a position corresponding to the center of the straight tubular part of the balloon 10.

The balloon 10 has a longitudinal direction and a radial direction, and is formed in a cylindrical shape having openings on the proximal side and the distal side (see FIG. 2). The radial direction of the balloon 10 means a direction perpendicular to the longitudinal direction and extending radially from the center of the balloon 10. The balloon 10 also has a circumferential direction, which is a direction along an outer periphery of the balloon 10 in an expanded state in a cross section perpendicular to the longitudinal direction of the balloon 10.

The balloon 10 comprises a straight tubular part 13, a proximal tapered part 12 located proximal to the straight tubular part 13, and a distal tapered part 14 located distal to the straight tubular part 13 in the longitudinal direction. The straight tubular part 13 is formed in a substantially cylindrical shape extending in the longitudinal direction, and is formed with the largest length in the radial direction (namely, the largest outer diameter) in the balloon 10. The proximal tapered part 12 is located proximal to the straight tubular part 13 and is connected to a proximal end of the straight tubular part 13. The proximal tapered part 12 is formed such that the outer diameter becomes smaller with increasing distance from the straight tubular part 13. The distal tapered part 14 is located distal to the straight tubular part 13 and is connected to a distal end of the straight tubular part 13. The distal tapered part 14 is formed such that the outer diameter becomes smaller with increasing distance from the straight tubular part 13. The balloon 10 may further comprise a proximal sleeve part 11 located proximal to the proximal tapered part 12 and a distal sleeve part 15 located distal to the distal tapered part 14. The proximal sleeve part 11 is located proximal to the proximal tapered part 12 and is connected to a proximal end of the proximal tapered part 12. The proximal sleeve part 11 is formed in a substantially cylindrical shape. The distal sleeve part 15 is located distal to the distal tapered part 14 and is connected to a distal end of the distal tapered part 14. The distal sleeve part 15 is formed in a substantially cylindrical shape.

By configuring the balloon 10 as described above, when the balloon 10 is inflated at a stenosis site, the straight tubular part 13 comes into sufficient contact with the stenosis site, making it easier to perform treatment such as expanding the stenosis site. In addition, since the balloon 10 has the proximal tapered part 12 and the distal tapered part 14, when the balloon 10 is deflated and the outer diameters of the proximal and distal ends of the balloon 10 are reduced, the step between the shaft 2 and the balloon 10 can be reduced, making it easy to insert the balloon 10 into a body cavity or a forceps channel of an endoscope.

In the distal part of the shaft 2, it may be preferable that the inner shaft 3 extends distally from the distal end of the outer shaft 4 and extends through the internal space of the balloon 10 from the proximal sleeve part 11 to the distal sleeve part 15. And, it may be preferable that the outer surface of the inner shaft 3 is joined to the inner surface of the distal sleeve part 15 of the balloon 10, and that the outer surface of the outer shaft 4 is joined to the inner surface of the proximal sleeve part 11 of the balloon 10. By configuring the distal part of the shaft 2 in this manner, the balloon expansion fluid can be supplied to the internal space of the balloon 10 through the space between the inner shaft 3 and the outer shaft 4.

The balloon 10 may be made of resin, and the resin may be thermoplastic resin. This makes it easy to manufacture the balloon 10 by molding. Examples of resin constituting the balloon 10 include polyolefin resins such as polyethylene, polypropylene and ethylene-propylene copolymers, polyester resins such as polyethylene terephthalate and polyester elastomers, polyurethane resins such as polyurethane and polyurethane elastomers, polyphenylene sulfide resins, polyamide resins such as polyamide and polyamide elastomers, fluororesins, silicone resins, natural rubbers such as latex rubber, and others. These may be used alone or in combination of two or more. Among them, polyamide resins, polyester resins, and polyurethane resins may be used. In particular, elastomer resins may be used in terms of thinning and flexibility of the balloon 10. For example, among polyamide resins, nylon 12, nylon 11 and the like are suitable materials for the balloon 10, and nylon 12 may be used since they can be relatively easily molded during blow molding. In addition, polyamide elastomers such as polyether ester amide elastomers and polyamide ether elastomers may be used in terms of thinning and flexibility of the balloon 10. Among them, polyether ester amide elastomers may be used since they have high yield strength and provide good dimensional stability to the balloon 10.

The balloon 10 has a convex strip 17 on the outer surface of the straight tubular part 13. By providing the convex strip 17 on the outer surface of the straight tubular part 13, the balloon 10 comes to have a scoring function, and when the balloon 10 is inflated at a stenosis site of a blood vessel, the convex strip 17 is capable of biting into a calcified stenosis site to make a crack in the stenosis site. Therefore, the stenosis site can be expanded while suppressing dissection of a vascular intima. It is also possible to increase the strength of the balloon 10 and suppress overexpansion of the balloon 10 when it is pressurized. The balloon 10 can also be used to treat stenosis or lesions in body cavities other than blood vessels, but the following description focuses on the application of the balloon 10 to a stenosis site in a blood vessel.

Figure 5:
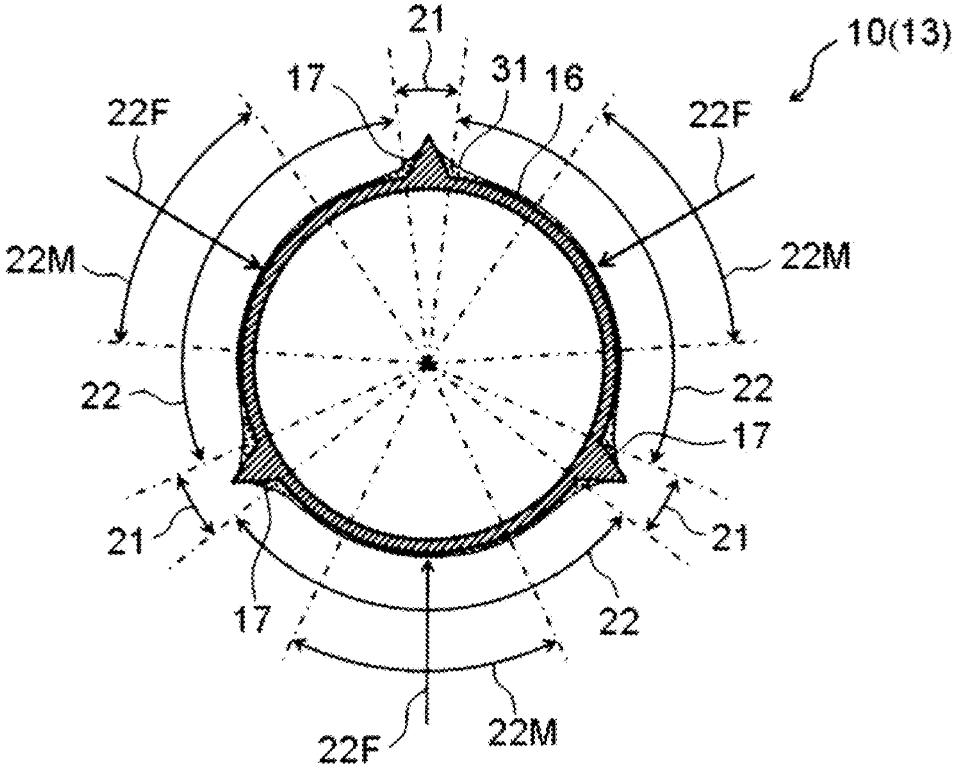
FIG. 5 shows an example of a cross-sectional view, taken perpendicular to a longitudinal direction, of a straight tubular part of the balloon provided with a drug layer.
Figure 6:
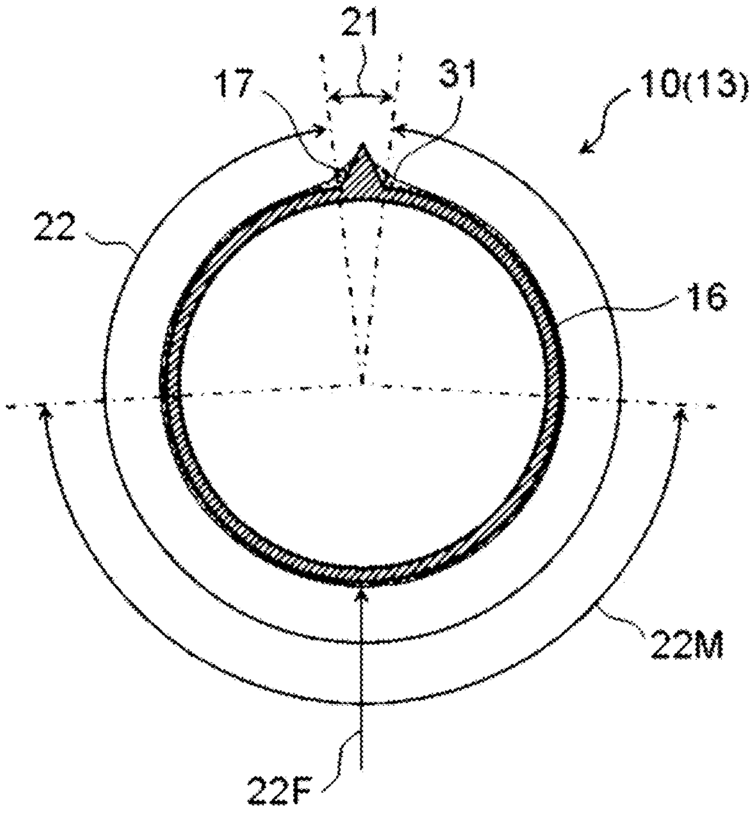
FIG. 6 shows another example of a cross-sectional view, taken perpendicular to a longitudinal direction, of a straight tubular part of the balloon provided with a drug layer.
Figure 7:
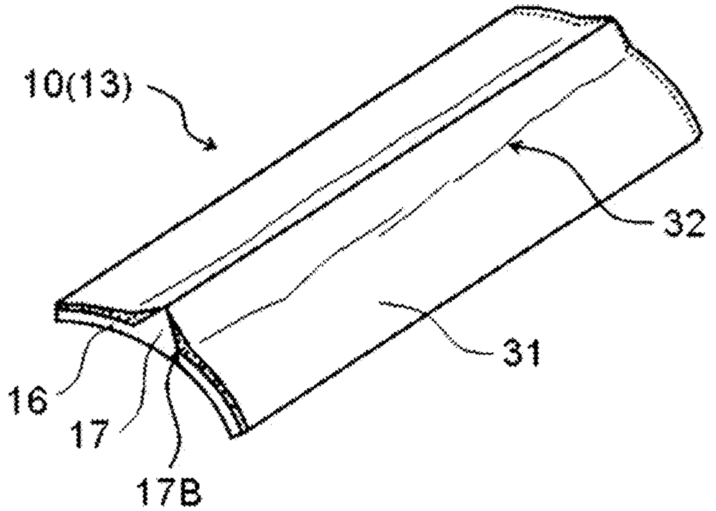
FIG. 7 shows a partial perspective view of the appearance of a straight tubular part of the balloon provided with a drug layer.

The convex strip 17 of the balloon 10 is explained in detail with reference to FIGS. 5 to 11. FIGS. 5 and 6 show cross-sectional views, taken perpendicular to the longitudinal direction, of the straight tubular part 13 of the balloon 10, FIG. 7 shows a partial perspective view of the appearance of the straight tubular part 13 of the balloon 10, and FIGS. 8 to 11 show enlarged cross-sectional views around the convex strip 17 of the balloon 10. FIGS. 5 to 11 show the balloon 10 with a drug layer 31 retained on the outer surface of the straight tubular part 13. FIG. 5 shows an example of the configuration in which a drug layer 31 is provided on the outer surface of the balloon 10 shown in FIGS. 2 and 4, and the convex strips 17 are provided at three locations in the circumferential direction of the straight tubular part 13. FIG. 6 shows an example of the configuration in which the convex strip 17 is provided at one location in the circumferential direction of the straight tubular part 13, and a drug layer 31 is provided on the outer surface of the balloon 10.

The straight tubular part 13 of the balloon 10 comprises a balloon body 16 of a cylindrical shape, and the convex strip 17 is provided on the outer surface of the balloon body 16. The convex strip 17 is provided so as to protrude outwards in the radial direction from the outer surface of the balloon body 16. In the balloon 10 being provided with the convex strip 17, a convex strip-present region 21 and a convex strip-absent region 22 are formed on the outer surface of the straight tubular part 13.

The convex strip 17 has an apex 17A and a base 17B (see FIGS. 8 to 11). In the convex strip 17, the apex 17A refers to a top of the convex strip 17, namely, a part located most outward in the radial direction of the convex strip 17, and the base 17B refers to a boundary with the balloon body 16 on a lateral surface 18 of the convex strip 17, namely, a part located most inward in the radial direction of the convex strip 17.

The convex strip 17 can be made of, for example, resin. When the convex strip 17 is made of resin, the balloon 10 having the convex strip 17 can be manufactured by molding a resin, making manufacturing easier. In this case, the convex strip 17 and the balloon body 16 may be made of the same resin, and the convex strip 17 and the balloon body 16 may be integrally formed. The balloon body 16 may have an inner layer and an outer layer, and in this case, the convex strip 17 may be made of the same resin as the outer layer of the balloon body 16. This makes it less likely that the convex strip 17 falls off the balloon body 16 unintentionally. Alternatively, the convex strip 17 and the balloon body 16 may be made of different resins from each other, so long as there is a certain degree of compatibility between the resin constituting the convex strip 17 and the resin constituting the balloon body 16.

The convex strip 17 may be made of metal, or may be made of a combination of metal and resin. In the latter case, it may be preferable that a portion including the apex 17A of the convex strip 17 is made of metal. This makes it easy for the convex strip 17 to crack or cut open a stenosis site when the balloon 10 is inflated. For example, the entire convex strip 17 may be made of metal, or a portion including the base 17B of the convex strip 17 may be made of resin and a portion including the apex 17A of the convex strip 17 may be made of metal. Therefore, it may be preferable that the convex strip 17 is made of resin, metal, or a combination thereof.

In the straight tubular part 13, the balloon body 16 is defined as a part having a cylindrical shape. A portion of the straight tubular part 13 excluding the convex strip 17 which protrudes outwards in the radial direction comes to be the balloon body 16. The balloon body 16 can be considered to have a cylindrical outer surface. Therefore, in a cross section, perpendicular to the longitudinal direction, of the straight tubular part 13, the outer shape of the balloon body 16 is formed to be substantially circular, which makes it possible to distinguish the balloon body 16 and the convex strip 17. In FIGS. 8 to 11, the balloon body 16 and the convex strip 17 are separated by dotted lines. The convex strip-present region 21 consists of the balloon body 16 and the convex strip 17, and the convex strip-absent region 22 consists of the balloon body 16.

The convex strip 17 is provided in the form of a ridge on the outer surface of the straight tubular part 13. The convex strip 17 may be disposed so as to extend in the longitudinal direction. In this case, the convex strip 17 may extend approximately parallel to the longitudinal direction of the balloon 10, or may extend in a spiral shape in the longitudinal direction. In view of enhancing a scoring function of the balloon 10 and facilitating the manufacture of a balloon 10 having the convex strip 17c. it may be preferable that the convex strip 17 extends approximately parallel to the longitudinal direction of the balloon 10.

In the cross section perpendicular to the longitudinal direction of the straight tubular part 13, only one convex strip 17 may be provided, or a plurality of the convex strips 17 may be provided. In the case where only one convex strip 17 is provided in the straight tubular part 13, only one convex strip-absent region 22 is formed in the straight tubular part 13, and in the case where a plurality of the convex strips 17 are provided in the straight tubular part 13, a plurality of convex strip-absent regions 22 are formed in the straight tubular part 13. The number of the convex strip-absent region 22 is equal to the number of the convex strip 17. In FIG. 5, the convex strips 17 are provided at three locations in the circumferential direction of the straight tubular part 13 of the balloon 10, and in FIG. 6, the convex strip 17 is provided at only one location in the circumferential direction of the straight tubular part 13 of the balloon 10.

It may be preferable that a plurality of the convex strips 17 are provided at different positions in the circumferential direction in the straight tubular part 13 of the balloon 10. That is, the convex strips 17 may be provided at multiple locations in the circumferential direction of the balloon 10. In this case, the convex strips 17 may be arranged at approximately equal intervals in the circumferential direction of the straight tubular part 13 of the balloon 10. This makes it possible to make cracks in multiple locations in a stenosis site when the balloon 10 is inflated. The convex strips 17 may be provided at two or more locations in the circumferential direction of the balloon 10, or at three or more locations, and at eight or less locations, or at six or less locations. In this case, the interval between the convex strips 17 in the circumferential direction may be longer than the length of the single convex strip 17 in the circumferential direction.

The cross-sectional shape of the convex strip 17 is not particularly limited. For example, the shape of the convex strip 17 in a cross section perpendicular to the longitudinal direction of the straight tubular part 13 may be a polygonal shape such as a triangle or a rectangle, a partial shape of a circle such as a semicircle or a sector, an approximately circular shape, a wedge shape, a convex shape, a spindle shape, an indefinite shape, or the like. The polygonal shape includes rounded polygons with rounded corners, and polygons with at least some of the sides being curved, in addition to polygons with clear corner apexes and straight sides. The convex strip 17 may be formed so as to narrow toward the apex 17A.

Figure 8:
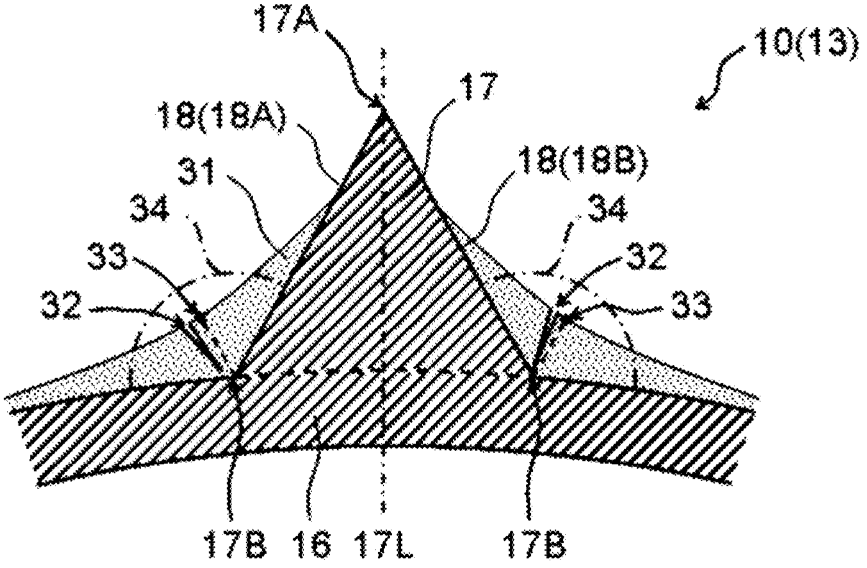
FIG. 8 shows an enlarged cross-sectional view around a convex strip in the balloon shown in FIGS. 5 and 6.
Figure 9:
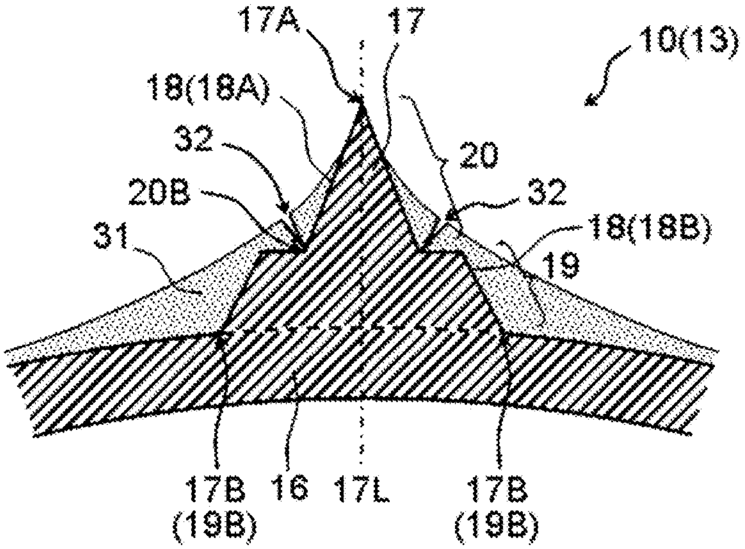
FIG. 9 shows an example of an enlarged cross-sectional view around a convex strip in the balloon provided with a drug layer.
Figure 10:
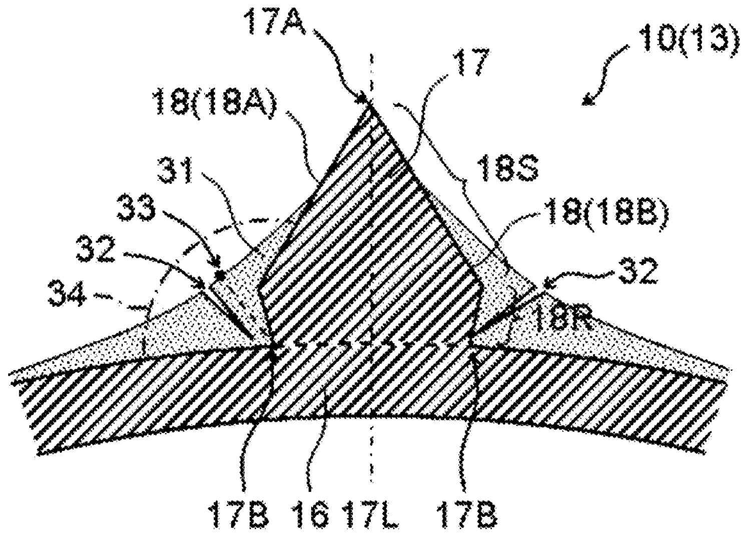
FIG. 10 shows another example of an enlarged cross-sectional view around a convex strip in the balloon provided with a drug layer.

FIGS. 8 to 10 show examples of various cross-sectional shapes of the convex strip 17. In FIG. 8, the convex strip 17 is formed so that its width narrows steplessly toward the apex 17A. In FIG. 9, the convex strip 17 is formed in multiple steps, and is formed so that its width narrows stepwise toward the apex 17A. In FIG. 10, the convex strip 17 is formed so as to have a portion that widens toward the apex 17A and a portion that narrows toward the apex 17A. Details of each embodiment of the convex strips 17 shown in FIGS. 8 to 10 are described later.

In the cross section perpendicular to the longitudinal direction of the straight tubular part 13, the height of the convex strip 17 can be, for example, 0.2 times or more the width (maximum width) of the convex strip 17. In the convex strip 17 formed in this manner, when the balloon 10 is expanded at a stenosis site, the convex strip 17 can easily bite into the stenosis site and the scoring function of the convex strip 17 can be improved. The width of the convex strip 17 described here means the length of the convex strip 17 in the circumferential direction. The convex strip 17 may be formed to have a maximum width at the base 17B, thereby allowing the convex strip 17 to be stably installed on the outer surface of the balloon body 16. In view of making it easier to form a crack extending along the base 17B of the convex strip 17 when a drug layer 31 is provided on a lateral surface 18 of the convex strip 17 as described later, the height of the convex strip 17 may be 0.4 times or more, or 0.7 times or more the width of the convex strip 17. Meanwhile, in view of stably installing the convex strip 17 on the outer surface of the straight tubular part 13, the height of the convex strip 17 may be 2.0 times or less, 1.8 times or less, or 1.5 times or less the width of the convex strip 17.

In the straight tubular part 13, the thickness of a part where the convex strip 17 is provided, namely, the thickness of the convex strip-present region 21, may be formed thicker than the thickness of a part where the convex strip 17 is not provided, namely, the thickness of the convex strip-absent region 22. This can improve the scoring function of the convex strip 17. The thickness (maximum thickness) of the convex strip-present region 21 may be 1.5 times or more, 2.0 times or more, or 2.5 times or more the thickness of the convex strip-absent region 22. The upper limit of the thickness of the convex strip-present region 21 is not particularly limited, and may be, for example, 30 times or less, 20 times or less, or 10 times or less the thickness of the convex strip-absent region 22.

In the balloon 10, the convex strip 17 may be provided over at least ½ of the longitudinal length of the straight tubular part 13, over at least ⅔ of the longitudinal length of that, or over at least ¾ of the longitudinal length of that. This makes it possible to crack a stenosis site over a wide area when the balloon 10 is expanded. The convex strip 17 may also be provided on the outer surface of the proximal tapered part 12 and/or the distal tapered part 14. In FIGS. 1 and 2, the convex strips 17 are provided so as to extend from the proximal tapered part 12 to the distal tapered part 14 via the straight tubular part 13.

In the balloon 10, an inner convex strip that protrudes inward in the radial direction on the inner surface of the balloon 10 may be provided (not shown). The convex strip 17 and the inner convex strip may be located at the same position in the longitudinal direction or circumferential direction of the balloon 10, and may be integrally formed, and thereby a part of the balloon 10 may be formed to be thick.

A drug layer 31 is provided on the outer surface of the straight tubular part 13 of the balloon 10. A drug contained in the drug layer 31 is not particularly limited as long as it is a pharmacologically active substance, and examples of the drug include drugs that are acceptable as medicines, such as gene therapy drugs, non-gene therapy drugs, small molecules, and cells. In particular, in the case of using the balloon catheter 1 for the purpose of suppressing restenosis of blood vessels after treatment in angioplasty, anti-restenosis drugs such as antiproliferative drugs and immunosuppressants can be used as the drug, and specifically, drugs such as paclitaxel, sirolimus (rapamycin), everolimus, and zotarolimus can be used. These drugs may be used alone or in combination of two or more.

The drug layer 31 may contain an auxiliary agent for improving dispersibility, solubility, migration to a blood vessel wall, or storage stability of the drug, in addition to the pharmacologically active substance. Examples of the auxiliary agent include a stabilizer, a binder, a disintegrant, a moisture-proofing agent, a preservative, a dissolution aid, and others; and specific examples thereof include lactose, sucrose, maltose, dextrin, xylitol, erythritol, mannitol, ethylenediamine, potassium iodide, urea, polysorbate, dibutylhydroxytoluene, polyethylene glycol, lipids, sodium pyrosulfite, ascorbic acid, tocopherol, benzoic acid, paraoxybenzoic acid esters, polyacrylic acid, polylactic acid, polyglycolic acid, hyaluronic acid, chitosan, gelatin, and others The drug layer 31 may include a protective layer to prevent the drug from dissolving or falling off in blood during delivery to a stenosis site. It may be preferable that the protective layer is included as part of the drug layer 31 and constitutes the outermost layer of the drug layer 31. The protective layer is made of, for example, a water-soluble polymer, and can be formed from, for example, carboxymethylcellulose, hydroxypropylcellulose, methylcellulose, hydroxyethylcellulose, polyvinyl alcohol, alginic acid, pectin, gum arabic, gellan gum, guar gum, xanthan gum, carrageenan, gelatin or the like.

The drug constituting the drug layer 31 may be crystalline, and for example, the pharmacologically active substance may be crystalline. Examples of the crystalline pharmacologically active substance include paclitaxel, sirolimus (rapamycin), everolimus, zotarolimus, and others. Such substance increases the brittleness of the drug layer 31, making the drug layer 31 more likely to peel off from the outer surface of balloon 10 when balloon 10 is inflated. It may also be preferable that the auxiliary agent or protective agent contained together with the pharmacologically active substance is crystalline. Examples of the crystalline auxiliary agent and protective agent include sugar, urea, salts such as potassium iodide, ascorbic acid, polylactic acid, polyglycolic acid, and others.

The drug layer 31 is provided on the outer surface of the straight tubular part 13 including the lateral surface 18 of the convex strip 17. By providing the drug layer 31 in this manner, the drug can be efficiently transferred to the inner surface of a blood vessel wall and further to the inside of the blood vessel wall when the balloon 10 is inflated at a stenosis site. That is, when the balloon 10 is inflated at a stenosis site, the convex strip 17 bites into the stenosis site and effectively expands the stenosis site, as well as the drug layer 31 provided on the lateral surface 18 of the convex strip 17 can be transferred to a blood vessel wall at the expanded stenosis site. The drug layer 31 may be disposed from the convex strip-absent region 22 to the lateral surface 18 of the convex strip 17.

As shown in FIGS. 7, 8, 10 and 11, the balloon 10 is configured such that a crack 32 is formed on the surface of the drug layer 31 so as to extend along the base 17B of the convex strip 17. As the crack 32 is formed on the surface of the drug layer 31 in this manner, when the balloon 10 is inflated at a stenosis site and the drug layer 31 comes into contact with the inner surface of a blood vessel wall, the drug layer 31 provided on the lateral surface 18 of the convex strip 17 is more likely to peel off from the surface of the balloon 10 starting from the crack 32, and the drug layer 31 is more likely to be transferred from the surface of the balloon 10 to the blood vessel wall.

In the case where the convex strip 17 is formed in multiple steps as shown in FIG. 9, it is sufficient that the crack 32 is formed on the surface of the drug layer 31 so as to extend along the base of any step of the multi-step convex strip 17. In FIG. 9, the multi-step convex strip 17 has a first step 19 adjacent to the outer surface of the balloon body 16 and a second step 20 on the apex 17A side of the first step 19, and it is sufficient that the crack 32 may be formed on the surface of the drug layer 31 so as to extend along at least one of the base 19B of the first stage 19 and the base 20B of the second stage 20. FIG. 9 shows an example in which the crack 32 extending along the base 20B of the second step 20 is formed on the surface of the drug layer 31. The base 19B of the first step 19 of the convex strip 17 corresponds to the base 17B of the convex strip 17.

Hereinafter, the crack 32 on the drug layer 31 is explained in detail referring to the example in which the crack 32 is formed on the surface of the drug layer 31 along the base 17B of the convex strip 17; however, the following description also applies to the case in which the crack 32 is formed on the surface of the drug layer 31 along the base of any step of the multi-step convex strip 17.

As viewed from the outside of the balloon 10, the crack 32 is formed on the surface of the drug layer 31 so as to extend along the extending direction of the base 17B, that is, along the extending direction of the boundary between the convex strip-present region 21 and the convex strip-absent region 22 (see FIG. 7). The crack 32 may be formed so as to extend parallel to the extending direction of the base 17B, or at least a part of the crack 32 may be formed so as to extend obliquely to the extending direction of the base 17B.

It is sufficient that the crack 32 is formed to extend along the extending direction of the base 17B as a whole. The crack 32 may be formed to extend continuously or may be formed to extend intermittently along the base 17B. In addition, a plurality of the cracks 32 extending along the base 17 may be formed so as to be lined up in the circumferential direction, that is, so as to overlap in the longitudinal direction. For example, a part of one of the plurality of cracks 32 and a part of another of the plurality of cracks 32 may be formed so as to overlap with each other in the longitudinal direction of the balloon 10.

The crack 32 may be formed over at least ½ of the longitudinal length of the drug layer 31 in the straight tubular part 13, over at least ⅔ of the longitudinal length of that, or over at least ¾ of the longitudinal length of that. The crack 32 may be formed over the entire longitudinal length of the drug layer 31 in the straight tubular part 13.

In the cross section perpendicular to the longitudinal direction of the straight tubular part 13, the crack 32 may be formed on the surface of the drug layer 31 at or near the shortest point 33 from the base 17B. Specifically, in the cross section perpendicular to the longitudinal direction of the straight tubular part 13, a straight line is drawn connecting the base 17B of the convex strip 17 to the shortest point 33 on the surface of the drug layer 31, and assuming that the length of the straight line from the base 17B to the shortest point 33 is R, the crack 32 on the surface of the drug layer 31 may be located within a virtual circle 34 having a radius of 1.5R centered on the base 17B in the cross section perpendicular to the longitudinal direction of the straight tubular part 13. In the cross section perpendicular to the longitudinal direction of the straight tubular part 13, the entire crack 32 may be located within the virtual circle 34 having a radius of 1.5R centered on the base 17B. In FIGS. 8 to 11, a portion of the virtual circle 34 having a radius of 1.5R centered on the base 17B is shown by a dashed line. The radius of the virtual circle 34 may be 1.3R.

In the cross section perpendicular to the longitudinal direction of the straight tubular part 13, the crack 32 may be formed so as to extend from the surface of the drug layer 31 to the outer surface of the straight tubular part 13 of the balloon 10, or may be formed so as to extend from the surface of the drug layer 31 to the inside of the drug layer 31 as an end point.

The number of the bases 17B of the convex strip 17 in the cross section perpendicular to the longitudinal direction of the straight tubular part 13 is twice the number of convex strip 17, that is, the sum of the number of bases 17B on a first lateral surface 18A and the number of bases 17B on a second lateral surface 18B of each convex strip 17; and in the straight tubular part 13 of the balloon, it is sufficient that the crack 32 is formed on the drug layer 31 along at least one of the plurality of bases 17B of the convex strip 17. Regarding the first lateral surface 18A and the second lateral surface 18B of the convex strip 17, the lateral surface 18 on one side of an imaginary straight line 17L that passes through the apex 17A of the convex strip 17 and extends in the radial direction is the first lateral surface 18A, and the lateral surface 18 on the other side of the imaginary straight line 17L is the second lateral surface 18B, in the cross section perpendicular to the longitudinal direction of the straight tubular part 13. For example, as viewed from the distal side of the balloon 10, the lateral surface 18 on the left side of the convex strip 17 can be the first lateral surface 18A, and the lateral surface 18 on the right side can be the second lateral surface 18B.

In the case where a plurality of the convex strips 17 are provided, in the cross section perpendicular to the longitudinal direction of the straight tubular part 13, a plurality of the convex strip-absent regions 22 are formed on the outer surface of the straight tubular part 13 by the plurality of convex strips 17, and it is sufficient that the crack 32 is formed on the drug layer 31 along at least one of the plurality of bases 17B of the convex strip 17. The crack 32 may be formed on the drug layer 31 along the base 17B of at least one of the first lateral surface 18A and the second lateral surface 18B of each convex strip 17, or the cracks 32 may be formed on the drug layer 31 along the bases 17B of both the first lateral surface 18A and the second lateral surface 18B of each convex strip 17.

It may be preferable that the drug layer 31 is formed relatively thick at the base 17B of the convex strip 17. For example, in the balloon 10, in the cross section perpendicular to the longitudinal direction of the straight tubular part 13, the thickness of the drug layer 31 at the base 17B of the convex strip 17 may be formed thicker than the thickness of the drug layer 31 at the farthest point 22F from the convex strip 17 in the convex strip-absent region 22. By providing the drug layer 31 in this manner, the drug layer 31 is present at a thicker thickness at the base 17B of the convex strip 17, and as a result, when the balloon 10 is inflated at a stenosis site, a larger amount of the drug can be delivered to the inner surface of a blood vessel wall and further to the inside of the blood vessel wall in the expanded stenosis site.

The thickness of the drug layer 31 at the base 17B of the convex strip 17 means the length of a straight line from the base 17B of the convex strip 17 to the shortest point 33 on the surface of the drug layer 31, provided that the straight line is drawn from the base 17B of the convex strip 17 to the shortest point 33 on the surface of the drug layer 31 in the cross section perpendicular to the longitudinal direction of the straight tubular part 13. The shortest point 33 means the shortest point from the base 17B to the surface of the drug layer 31, excluding a part where the crack 32 is formed. Thus, the thickness of the drug layer 31 at the base 17B of the convex strip 17 means the thickness of the drug layer 31 excluding the part where the crack 32 is formed.

The thickness of the drug layer 31 at the farthest point 22F from the convex strip 17 in the convex strip-absent region 22 means the length in the radial direction from the outer surface of the balloon body 16 to the surface of the drug layer 31 at the farthest point 22F. In the case where the drug layer 31 does not exist at the farthest point 22F from the convex strip 17 in the convex strip-absent region 22, the thickness of the drug layer 31 at the farthest point 22F is 0.

The farthest point 22F from the convex strip 17 in the convex strip-absent region 22 is determined as follows. In the case where only one convex strip 17 is provided in the cross section perpendicular to the longitudinal direction of the straight tubular part 13 as shown in FIG. 6, a symmetrical point of the convex strip 17 in the circumferential direction of the straight tubular part 13 (that is, a symmetrical point with respect to the center of the balloon body 16 of a cylindrical shape) becomes the farthest point 22F from the convex strip 17 in the convex strip-absent region 22. In the case where a plurality of the convex strips 17 are provided in the cross section perpendicular to the longitudinal direction of the straight tubular part 13 as shown in FIG. 5, a midpoint, with respect to the circumferential direction, of the convex strips 17 adjacent to each other in the circumferential direction of the straight tubular part 13 becomes the farthest point 22F from the convex strips 17 in the convex strip-absent region 22.

This will be explained in more detail. The convex strip 17 has bases 17B of the convex strip 17 on each of the first lateral surface 18A and the second lateral surface 18B, and in the case where only one convex strip 17 is provided in the cross section perpendicular to the longitudinal direction of the straight tubular part 13 as shown in FIG. 6, a midpoint between the base 17B of the first lateral surface 18A and the base 17B of the second lateral surface 18B of the convex strip 17 in the convex strip-absent region 22 becomes the farthest point 22F from the convex strip 17 in the convex strip-absent region 22. In the case where a plurality of the convex strips 17 are provided in the cross section perpendicular to the longitudinal direction of the straight tubular part 13 as shown in FIG. 5, a midpoint between the base 17B of the first lateral surface 18A of one convex strip 17 and the base 17B of the second lateral surface 18B of the convex strip 17 adjacent to the first lateral surface 18A of the one convex strip 17 across the convex strip-absent region 22 becomes the farthest point 22F from the convex strip 17 in the convex strip-absent region 22.

In the straight tubular part 13 of the balloon, it may be preferable that the thickness of the drug layer 31 at at least one base 17B among a plurality of the bases 17B of the convex strip 17 is formed thicker than the thickness of the drug layer 31 at the farthest point 22F from the convex strip 17 in the convex strip-absent region 22. In the case where a plurality of the convex strips 17 are provided in the cross section perpendicular to the longitudinal direction of the straight tubular part 13 and a plurality of the convex strip-absent regions 22 are formed on the outer surface of the straight tubular part 13 by the plurality of convex strips 17, the thickness of the drug layer 31 at at least one base 17B among a plurality of the bases 17B of the convex strips 17 may be thicker than the average of the thicknesses of the drug layers 31 at the farthest point 22F from the convex strip 17 in a plurality of the convex strip-absent regions 22, or may be thicker than each of the thicknesses of the drug layers 31 at the farthest point 22F from the convex strip 17 in a plurality of the convex strip-absent regions 22. Furthermore, the thickness of the drug layer 31 at the base 17B of at least one of the first lateral surface 18A and the second lateral surface 18B of each convex strip 17 may be thicker than the average of the thicknesses of the drug layers 31 at the farthest point 22F from the convex strip 17 in a plurality of the convex strip-absent regions 22, or may be thicker than each of the thicknesses of the drug layers 31 at the farthest point 22F from the convex strip 17 in a plurality of the convex strip-absent regions 22.

The thickness of the drug layer 31 at the base 17B of the convex strip 17 and the thickness of the drug layer 31 at furthest point 22F from the convex strip 17 in the convex strip-absent region 22 can be determined, for example, as follows. The balloon 10 is cut perpendicular to the longitudinal direction in the straight tubular part 13 and is held so that the balloon body 16 is in a substantially circular shape, and in this state, the thickness of the drug layer 31 at the base 17B of the convex strip 17 and the thickness of the drug layer 31 at the furthest point 22F from the convex strip 17 in the convex strip-absent region 22 are measured. Alternatively, the folded balloon 10 may be cut perpendicular to the longitudinal direction in the straight tubular part 13, the outer periphery of the convex strip-absent region 22 between the convex strips 17 of the folded balloon 10 is measured, a midpoint of the outer periphery between the convex strips 17 is set as the farthest point 22F, and the thickness of the drug layer 31 at the base 17B of the convex strip 17 and the thickness of the drug layer 31 at the farthest point 22F from the convex strip 17 in the convex strip-absent region 22 may be measured.

The thickness of the drug layer 31 at the base 17B of the convex strip 17 may be, for example, 1.5 times or more, 2.0 times or more, or 2.5 times or more, the thickness of the drug layer 31 at the farthest point 22F from the convex strip 17 in the convex strip-absent region 22. The upper limit of the ratio of the thickness of the drug layer 31 at the base 17B of the convex strip 17 to the thickness of the drug layer 31 at the farthest point 22F from the convex strip 17 in the convex strip-absent region 22 is not particularly limited, and the drug layer 31 may not exist or may exist at a very thin thickness at the farthest point 22F from the convex strip 17 in the convex strip-absent region 22. For example, the thickness of the drug layer 31 at the base 17B of the convex strip 17 may be 100 times or less, 50 times or less, 30 times or less, 20 times or less, or 10 times or less, the thickness of the drug layer 31 at the farthest point 22F from the convex strip 17 in the convex strip-absent region 22.

In the above case, it is sufficient that the balloon 10 is formed such that the thickness of the drug layer 31 at the base 17B of the convex strip 17 is thicker than the thickness of the drug layer 31 at the farthest point 22F from the convex strip 17 in the convex strip-absent region 22 in at least a part of the straight tubular part 13 in the longitudinal direction. The drug layer 31 may be formed in that manner in the area of at least a part of a central ½ region of the straight tubular part 13 in the longitudinal direction, in the area of more than half of the central ½ region of the straight tubular part 13 in the longitudinal direction, or in the area of more than ⅔ of the central ½ region of the straight tubular part 13 in the longitudinal direction. For example, provided that a relative longitudinal position of the straight tubular part 13 is set as 0% at the proximal end and 100% at the distal end, a positional range of 25% to 75% of the straight tubular part 13 is cut in the radial direction at six locations at 10% intervals, and the thickness of the drug layer 31 at each cut cross section is measured, it may be preferable that the drug layer 31 is formed in the above manner at three or more locations. Thereby, it is possible to determine that the thickness of the drug layer 31 at the base 17B of the convex strip 17 is thicker than the thickness of the drug layer 31 at farthest point 22F from convex strip 17 in the convex strip-absent region 22 in no less than half of the central ½ region of straight tubular part 13 in the longitudinal direction. The drug layer 31 may be formed such that the thickness of the drug layer 31 at the base 17B of the convex strip 17 is thicker than the thickness of the drug layer 31 at the farthest point 22F from the convex strip 17 in the convex strip-absent region 22 over the entire central ½ region of the straight tubular part 13 in the longitudinal direction, and may be formed in this manner over the entire straight tubular part 13 in the longitudinal direction.

In the various explanations regarding the formation of the drug layer 31 in the cross section perpendicular to the longitudinal direction of the straight tubular part 13 below, the above explanations regarding the formation of the drug layer 31 in the longitudinal direction of the straight tubular part 13 are also referred to.

It may also be preferable that, in the cross section perpendicular to the longitudinal direction of the straight tubular part 13, the thickness of the drug layer 31 at the base 17B of the convex strip 17 is thicker than the average thickness of the drug layer 31 in a central ½ region 22M of the convex strip-absent region 22 in the circumferential direction. The central ½ region 22M of the convex strip-absent region 22 in the circumferential direction refers to central two sections when the convex strip-absent region 22 is divided into four equal sections in the circumferential direction in one convex strip-absent region 22. In the case where a plurality of the convex strips 17 are provided in the cross section perpendicular to the longitudinal direction of the straight tubular part 13, the thickness of the drug layer 31 at the base 17B (the base 17B of at least one of the first lateral surface 18A and the second lateral surface 18B) of at least one convex strip 17 may be formed thicker than the average of the average thicknesses of the drug layers 31 in the central ½ regions 22M of a plurality of the convex strip-absent regions 22 in the circumferential direction, or thicker than each average thickness of the drug layers 31 in the central ½ regions 22M of the plurality of convex strip-absent regions 22 in the circumferential direction. Furthermore, the thickness of the drug layer 31 at the base 17B of at least one of the first lateral surface 18A and the second lateral surface 18B of each convex strip 17 may be formed thicker than the average of the average thicknesses of the drug layers 31 in the central ½ region 22M of a plurality of the convex strip-absent regions 22 in the circumferential direction, or thicker than each average thickness of the drug layer 31 in the central ½ region 22M of the plurality of convex strip-absent regions 22 in the circumferential direction.

The average thickness of the drug layer 31 in the central ½ region 22M of the convex strip-absent region 22 in the circumferential direction can be calculated by dividing the area of the drug layer 31 in the central ½ region 22M of the convex strip-absent region 22 in the circumferential direction by the length of the central ½ region 22M of the convex strip-absent region 22 in the circumferential direction, when the straight tubular part 13 is viewed in the cross section perpendicular to the longitudinal direction. The average thickness of the drug layer 31 in the central ½ region 22M of the convex strip-absent region 22 in the circumferential direction can be conveniently determined by cutting the balloon perpendicular to the longitudinal direction in the straight tubular part 13, taking a photograph of the cut cross section, and processing the image.

The thickness of the drug layer 31 at the base 17B of the convex strip 17 may be 1.3 times or more, 1.5 times or more, or 2.0 times or more, the average thickness of the drug layer 31 in the central ½ region 22M of the convex strip-absent region 22 in the circumferential direction. The upper limit of the ratio of the thickness of the drug layer 31 at the base 17B of the convex strip 17 to the average thickness of the drug layer 31 in the central ½ region 22M of the convex strip-absent region 22 in the circumferential direction is not particularly limited. For example, the thickness of the drug layer 31 at the base 17B of the convex strip 17 may be 100 times or less, 50 times or less, 30 times or less, 20 times or less, or 10 times or less, the average thickness of the drug layer 31 in the central ½ region 22M of the convex strip-absent region 22 in the circumferential direction.

It may be preferable that the drug layer 31 is provided not only in the convex strip-present region 21 (i.e., the lateral surface 18 of the convex strip 17) but also in the convex strip-absent region 22 on the outer surface of the straight tubular part 13. For example, the drug layer 31 may be provided in at least a part of the central ½ region 22M of the convex strip-absent region 22 in the circumferential direction, and the drug layer 31 may be provided at the farthest point 22F from the convex strip 17 in the convex strip-absent region 22. By providing the drug layer 31 in the convex strip-absent region 22, the drug can be delivered to a wide range of the inner wall of a blood vessel at a stenosis site when the balloon 10 is inflated at the stenosis site.

In one embodiment, as shown in FIGS. 8 and 9, the convex strip 17 may be formed to have a portion that narrows toward the apex 17A and not to have a portion that widens toward the apex 17A. In other words, with respect to an imaginary straight line 17L that passes through the apex 17A of the convex strip 17 and extends in the radial direction, the lateral surface 18 of the convex strip 17 may be formed to have a portion that approaches the imaginary straight line 17L toward the apex 17A and not to have a portion that leaving from the imaginary straight line 17L toward the apex 17A. When the convex strip 17 is formed in this manner, even if the convex strip 17 is strongly pressed against the inner wall of a blood vessel when expanding the balloon 10 at a stenosis site, the convex strip 17 can easily bite into the stenosis site without being bent. The convex strip 17 may be formed so as to narrow toward the apex 17A all the way from the base 17B to the apex 17A. That is, the lateral surface 18 of the convex strip 17 may be formed so as to approach the imaginary straight line 17 all the way from the base 17B to the apex 17A of the convex strip 17.

The convex strip 17 may be formed so as to narrow steplessly toward the apex 17A as shown in FIG. 8, or may be formed so as to narrow stepwise toward the apex 17A as shown in FIG. 9. In the former case, the lateral surface 18 of the convex strip 17 may be formed in a straight line extending obliquely with respect to the imaginary straight line 17L, or may be formed in a curved line bulging outwards in the radial direction (which may include a straight line portion), or may be formed in a curved line bulging inward in the radial direction (which may include a straight line portion), in the cross section perpendicular to the longitudinal direction of the straight tubular part 13. In the latter case, the convex strip 17 may have a portion that narrows stepwise toward the apex 17A at least in a part from the base 17B to the apex 17A.

in another embodiment, as shown in FIG. 10, the convex strip 17 may be formed to have a portion that widens toward the apex 17A, and on the apex 17A side of that portion, a portion that narrows toward the apex 17A. For example, in the cross section perpendicular to the longitudinal direction of the straight tubular part 13, with respect to the imaginary straight line 17L that passes through the apex 17A of the convex strip 17 and extends in the radial direction, the lateral surface 18 of the convex strip 17 may be formed to have a portion 18R that leaves from the imaginary straight line 17L toward the apex 17A and a portion 18S that approaches to the imaginary straight line 17L toward the apex 17A on the apex 17A side of the portion 18S. In this case, a part of the lateral surface 18 of the convex strip 17 is formed recessed. This allows a larger amount of the drug to be retained in the recessed portion of the lateral surface 18 of the convex strip 17. In the convex strip 17, the portion that widens toward the apex 17A, or the portion 18R where the lateral surface 18 of the convex strip 17 leaves from the imaginary straight line 17L toward the apex 17A, may be formed at at least a part of the 0% to 30% height of the convex strip 17, and may not be formed at the 50% to 100% height of the convex strip 17. This allows a larger amount of the drug to be retained at the base 17B of the convex strip 17.

Figure 11:
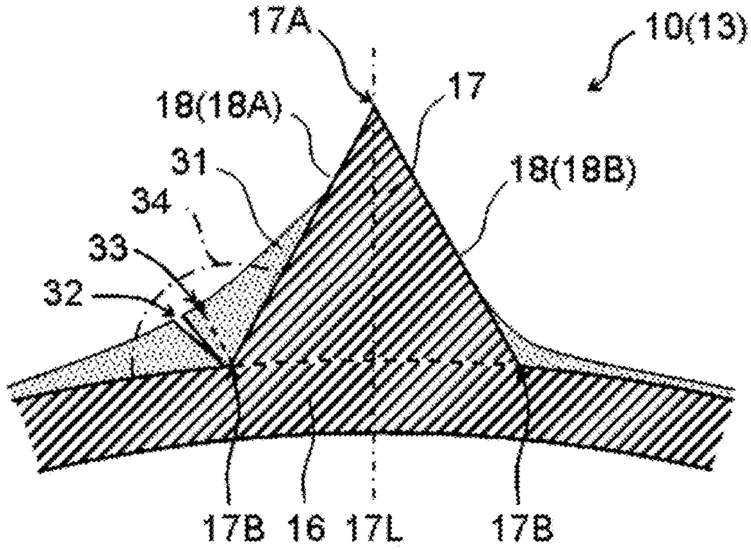
FIG. 11 shows another example of an enlarged cross-sectional view around a convex strip in the balloon provided with a drug layer.

As shown in FIG. 11, in the cross section perpendicular to the longitudinal direction of the straight tubular part 13, the thickness of the drug layer 31 at the base 17B of the first lateral surface 18A of the convex strip 17 may be formed thicker than the thickness of the drug layer 31 at the base 17B of the second lateral surface 18B of the convex strip 17.

When the drug layer 31 is formed on lateral surface 18 of convex strip 17 in this manner, the second lateral surface 18B of convex strip 17 is able to secure the ability to bite into a stenosis site, and a larger amount of the drug is retained on the first lateral surface 18A of convex strip 17. Therefore, when the balloon 10 is inflated at a stenosis site, the drug can be efficiently delivered to the stenosis site.

In delivering the balloon 10 to a treatment target such as a stenosis site of a blood vessel, it may be preferable that the balloon 10 is inserted in a guiding catheter or sheath in a contracted state. At this time, the balloon 10 may be folded appropriately so that its radial size is reduced.

Figure 12:
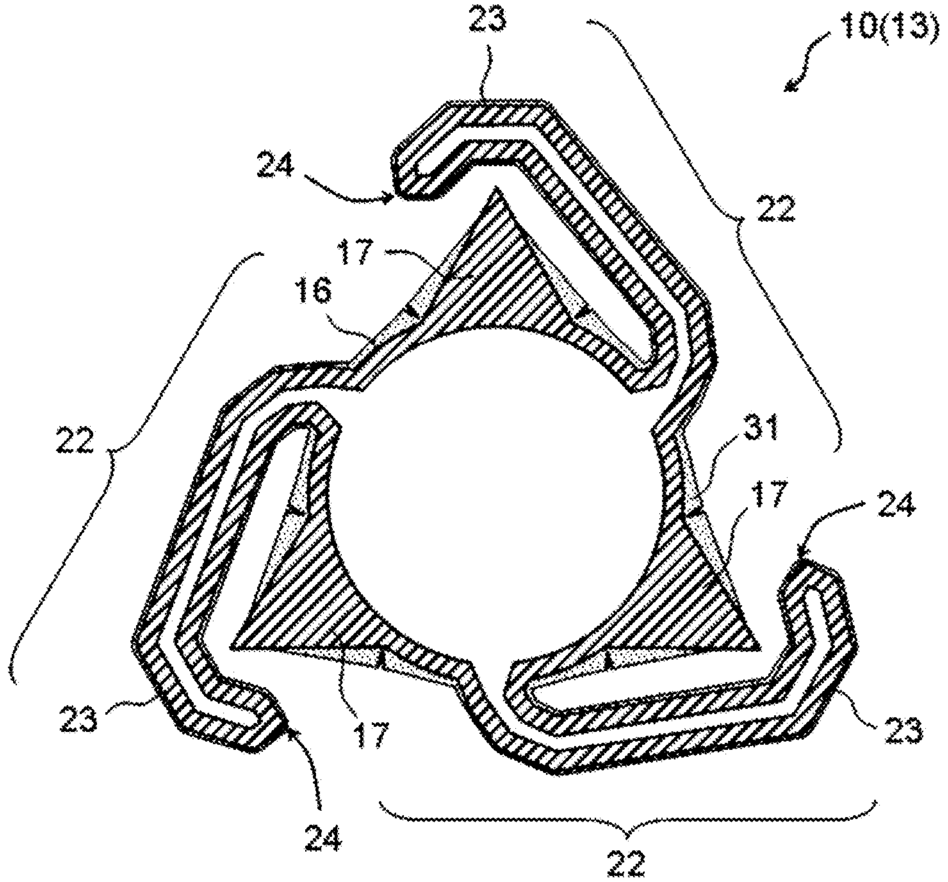
FIG. 12 shows an example of a cross-sectional view, taken perpendicular to a longitudinal direction, of the balloon shown in FIG. 5 in its contracted and folded state.
Figure 13:
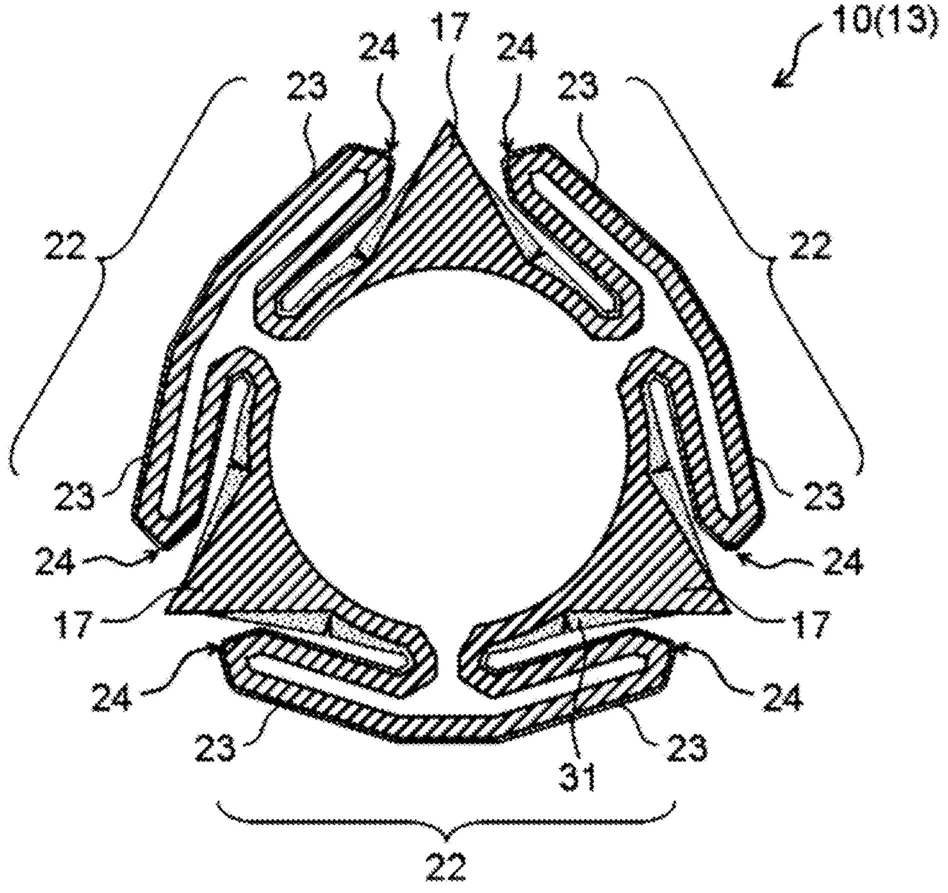
FIG. 13 shows another example of a cross-sectional view, taken perpendicular to a longitudinal direction, of the balloon shown in FIG. 5 in its contracted and folded state.

FIGS. 12 and 13 show examples of the balloon 10 shown in FIG. 5 being contracted and folded. As shown in FIGS. 12 and 13, in the contracted state of the balloon 10, it may be preferable that the straight tubular part 13 is folded back at the convex strip-absent region 22 with the inner surface of the balloon body 16 facing inwards to form a folded vane portion 23 in which the convex strip-absent regions 22 are laminated, and the folded vane portion 23 is arranged overlaying the outer surface of the straight tubular part 13. The folded vane portion 23 is formed by folding back the convex strip-absent region 22 of the balloon body 16 at a fold line 24, and the convex strip-absent regions 22 are overlapped with each other. At the fold line 24, the convex strip-absent region 22 is folded back with the inner surface of the balloon body 16 facing inwards. Therefore, the fold line 24 is formed as a mountain fold when viewed from the outside of the balloon 10. It may be preferable that the folded vane portion 23 is formed only from the convex strip-absent region 22 of the balloon body 16, and is not formed including the convex strip-present region 21.

It may be preferable that the fold line 24 is formed so as to extend approximately parallel to the extending direction of the convex strip 17. At the fold line 24, the convex strip-absent region 22 may be folded back so as to form a clear crease, or may be folded with a tip rounded. Note that the convex strip-absent region 22 of the balloon body 16 usually has a certain degree of thickness and elasticity, so that the convex strip-absent region 22 is folded back at the fold line 24 with the tip rounded. In this case, the tip where the convex strip-absent region 22 is folded back comes to be the fold line 24, as viewed in the cross section perpendicular to the longitudinal direction of the straight tubular part 13, In the straight tubular part 13, a fold line formed by folding back the balloon body 16 with the outer surface of the balloon body 16 facing inwards (that is, a valley fold line as viewed from the outside of the balloon 10) may be formed on one side and/or the other side of the fold line 24 in the circumferential direction. In this case, it may be preferable that the fold line of the valley fold line forms a base of the folded vane portion 23.

In one convex strip-absent region 22, only one fold line 24 may be formed, or two or more fold lines 24 may be formed. One or two fold lines 24 may be formed in one convex strip-absent region 22. In FIG. 12, one fold line 24 is formed in one convex strip-absent region 22, and in FIG. 13, two fold lines 24 are formed in one convex strip-absent region 22. In the case where only one fold line 24 is formed in one convex strip-absent region 22, it may be preferable that the folded vane portion 23 is inclined to one side in the circumferential direction as viewed in the cross section perpendicular to the longitudinal direction of the straight tubular part 13. In the case where two fold lines 24 are formed in one convex strip-absent region 22, it may be preferable that two folded vane portions 23 are inclined in opposite directions in the circumferential direction to each other and toward the convex strip 17 as viewed in the cross section perpendicular to the longitudinal direction of the straight tubular part 13. Thereby, the convex strip 17 is more easily protected by the folded vane portion 23 when the balloon 10 is in a contracted state.

In one embodiment, the folded vane portion 23 may be disposed to cover the apex 17A of the convex strip 17 when the balloon 10 is in a contracted state. In this case, the drug layer 31 provided on the convex strip 17 is protected by the folded vane portion 23, and for example, the drug layer 31 provided near the apex 17A of the convex strip 17 is more likely to be protected. Therefore, the drug layer 31 is less likely to fall off from the balloon 10 until the balloon 10 is delivered to a treatment target.

In another embodiment, the folded vane portion 23 may be disposed overlaying the outer surface of the straight tubular part 13 so as not to cover the apex 17A of the convex strip 17 when the balloon 10 is in a contracted state. In this case, when the balloon 10 is inflated at a stenosis site, the convex strip 17 quickly bite into the stenosis site, making it easier for the balloon 10 to effectively expand the stenosis site.

In FIG. 12, one folded vane portion 23 is formed in one convex strip-absent region 22, and the folded vane portion 23 is disposed so as to cover the apex 17A of the convex strip 17; nonetheless, in FIG. 12, the folded vane portion 23 may be disposed overlaying the outer surface of the straight tubular part 13 so as not to cover the apex 17A of the convex strip 17. In FIG. 13, two folded vane portions 23 are formed in one convex strip-absent region 22, and the folded vane portion 23 is disposed overlaying the outer surface of the straight tubular part 13 so as not to cover the apex 17A of the convex strip 17; nonetheless, the folded vane portion 23 may be disposed so as to cover the apex 17A of the convex strip 17.

Next, a method for manufacturing a balloon catheter of one or more embodiments of the present invention is described. A method for manufacturing a balloon catheter according to one or more embodiments of the present invention comprises the steps of: preparing a balloon having a convex strip on its outer surface (hereinafter referred to as a "balloon preparation step"), applying a drug solution to the outer surface of the balloon to form a drug layer (hereinafter referred to as a "drug layer forming step"), and bending the convex strip on the outer surface of the balloon body (hereinafter referred to as a "convex strip bending step").

In the balloon preparation step, the balloon 10 described above is prepared. Thus, the balloon 10 has a longitudinal direction extending from a proximal side to a distal side and a radial direction perpendicular to the longitudinal direction, and comprises a straight tubular part 13, a proximal tapered part 12 located proximal to the straight tubular part 13, and a distal tapered part 14 located distal to the straight tubular part 13, and the straight tubular part 13 comprises a balloon body portion 16 of a cylindrical shape and a convex strip 17 protruding outwards in the radial direction on the outer surface of the balloon body 16 and extending in the longitudinal direction. Details of the configuration and one or more embodiments of the balloon 10 are referred to the above description.

In the drug layer forming step, a drug solution is applied to the outer surface of the straight tubular part 13, including the lateral surface 18 of the convex strip 17, to form the drug layer 31. A method of applying the drug solution is not particularly limited, and for example, the drug solution may be applied to the outer surface of the straight tubular part 13 by using a brush, a spray, a coater or the like, or the drug solution may be applied to the outer surface of the straight tubular part 13 by immersing the balloon 10 in the drug solution. If necessary, the drug solution may be applied to the outer surface of the straight tubular part 13 after masking a part where the drug layer 31 is not to be formed.

Figure 14:
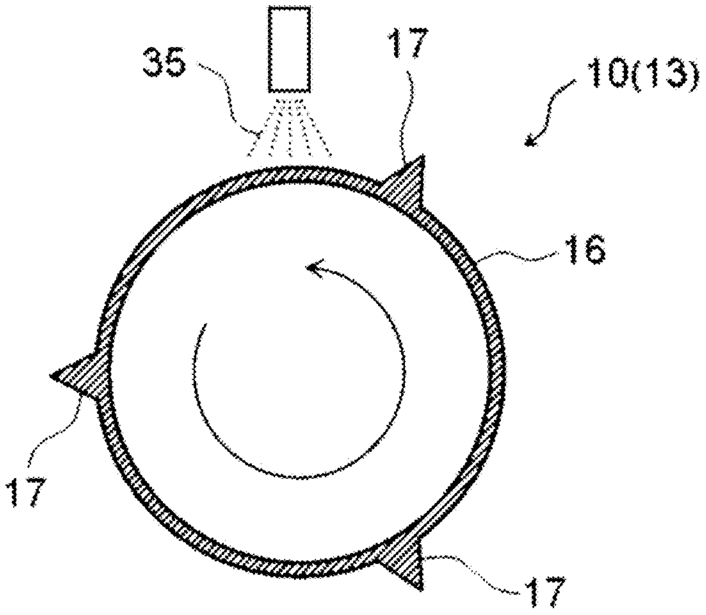
FIG. 14 shows a schematic diagram of a method of forming a drug layer on the surface of a balloon.

In view of facilitating forming the drug layer 31 on the lateral surface 18 of the convex strip 17, in the drug layer forming process, the drug solution 35 may be applied to the outer surface of the straight tubular part 13 of the balloon 10, and the balloon 10 may be rotated about a central axis extending in the longitudinal direction as shown in FIG. 14. FIG. 14 shows a cross sectional view of the balloon 10 shown in FIG. 2, taken perpendicular to the longitudinal direction, and shows a state in which the drug solution 35 is applied to the outer surface of the straight tubular part 13 of the balloon 10. When the drug solution 35 is applied to the outer surface of the straight tubular part 13 and the balloon 10 is rotated about the central axis extending in the longitudinal direction, the drug solution 35 applied to the outer surface of the straight tubular part 13, particularly the convex strip-absent region 22, moves circumferentially around the surface of the straight tubular part 13 and accumulates on the lateral surface 18 of the convex strip 17, resulting in a thicker drug layer 31 being formed on the lateral surface 18 and the base 17B of the convex strip 17.

The drug contained in the drug solution 35 is described above. The drug solution 35 may contain a solvent that dissolves or disperses the drug. The drug concentration of the drug solution 35 is not particularly limited, and the concentration may be adjusted appropriately so that the drug can be applied to the outer surface of the straight tubular part 13 and fluidity is ensured on the surface of the straight tubular part 13.

A method of applying the drug solution 35 is not particularly limited, but it may be preferable to apply the drug solution 35 to the outer surface of the straight tubular part 13 by spraying as shown in FIG. 14, which makes it easy to widely apply any amount of the drug solution 35 to the outer surface of the straight tubular part 13. It also makes it easy to form the drug layer 31 on the outer surface of the straight tubular part 13.

In the drug layer forming step, it may be preferable that the drug solution 35 is applied to the outer surface of the straight tubular part 13 in the state where the balloon 10 is expanded. It may also be preferable that the balloon 10 is rotated about the central axis extending in the longitudinal direction in the state where the balloon 10 is expanded. This facilitates the drug solution 35 applied to the convex strip-absent region 22 of the straight tubular part 13 to move circumferentially around the surface of the straight tubular part 13 and accumulate on the lateral surface 18 of the convex strip 17.

In the drug layer forming step, the drug solution 35 may be applied to the outer surface of the straight tubular part 13 while the balloon 10 is rotated about the central axis extending in the longitudinal direction, or after the drug solution 35 is applied to the outer surface of the straight tubular part 13, the balloon 10 may be rotated about the central axis extending in the longitudinal direction. In either case, the drug solution 35 applied to the outer surface of the straight tubular part 13 can move circumferentially around the surface of the straight tubular part 13 and accumulate at the base 17B of the convex strip 17.

In the drug layer forming step, the balloon 10 may be rotated in only one direction or may be rotated in both one direction and the opposite direction in turn, about the central axis extending in the longitudinal direction. By appropriately setting the rotating direction of the balloon 10, the thicknesses of the drug layers 31 formed at the base 17B of the first lateral surface 18A and the base 17B of the second lateral surface 18B of the convex strip 17 can be adjusted as desired.

In the drug layer forming step, it may be preferable to evaporate at least a part of the solvent contained in the drug solution 35 while rotating the balloon 10. This makes it easy to form the drug layer 31 on the outer surface of the straight tubular part 13. Evaporation of the solvent may be performed by heating the balloon 10 to which the drug solution 35 has been applied, by placing the balloon 10 to which the drug solution 35 has been applied in a reduced pressure state, or by blowing air on the balloon 10 to which the drug solution 35 has been applied. In addition, by selecting a solvent having an appropriate vapor pressure, the solvent may be allowed to evaporate naturally while rotating the balloon 10.

After the drug layer forming step, the convex strip bending step is performed, where the convex strip 17 is bent relative to the outer surface of the balloon body 16. In the convex strip bending step, the convex strip 17 is bent in the circumferential direction relative to the outer surface of the balloon body 16. This allows a crack 32 extending along the base 17B of the convex strip 17 to be formed on the surface of the drug layer 31. The convex strip 17 may be bent in only one circumferential direction, or may be bent in one circumferential direction and then in the other circumferential direction. In view of easily bending the convex strip 17 in the convex strip bending step, the height of the convex strip 17 may be 0.2 times or more, 0.4 times or more, or 0.7 times or more, the width of the convex strip 17.

This application claims priority to Japanese Patent Application No. 2022-183695, filed on Nov. 16, 2022. All of the contents of the Japanese Patent Application No. 2022-183695, filed on Nov. 16, 2022, are incorporated by reference herein.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

REFERENCE SIGNS LIST

- 1: balloon catheter
- 2: shaft
- 5: hub
- 10: balloon
- 11: proximal sleeve part
- 12: proximal tapered part
- 13: straight tubular part
- 14: distal tapered part
- 15: distal sleeve part
- 16: balloon body
- 17: convex strip, 17A: apex, 17B: base
- 18: lateral surface, 18A: first lateral surface, 18B: second lateral surface
- 19: first step
- 20: second step
- 21: convex strip-present region
- 22: convex strip-absent region
- 23: folded vane portion
- 24: fold line
- 31: drug layer 32: crack
35: drug solution

The invention claimed is:

1. A balloon for a balloon catheter, having a longitudinal direction extending from a proximal side to a distal side and a radial direction perpendicular to the longitudinal direction, comprising:
a straight tubular part comprising a balloon body of a cylindrical shape and a convex strip which protrudes outwards in the radial direction on an outer surface of the balloon body;
a proximal tapered part located proximal to the straight tubular part;
a distal tapered part located distal to the straight tubular part; and
a drug layer provided on the outer surface of the straight tubular part including a lateral surface of the convex strip, wherein a crack is formed on a surface of the drug layer extending along a base of the convex strip.

2. The balloon according to claim 1, wherein the convex strip extends in the longitudinal direction of the balloon.

3. The balloon according to claim 1, wherein:
the outer surface of the straight tubular part has a convex strip-present region where the convex strip is present and a convex strip-absent region where the convex strip is not present; and
a thickness of the drug layer at the base of the convex strip, excluding a part where the crack is formed, is thicker than a thickness of the drug layer at a farthest point from the convex strip in the convex strip-absent region in a cross section perpendicular to the longitudinal direction of the straight tubular part.

4. The balloon according to claim 1, wherein a drug constituting the drug layer is crystalline.

5. The balloon according to claim 1, wherein the convex strip is made of resin, metal, or a combination thereof.

6. The balloon according to claim 1, wherein:
the outer surface of the straight tubular part has a convex strip-present region where the convex strip is present and a convex strip-absent region where the convex strip is not present; and
in a contracted state of the balloon, the straight tubular part is folded back at the convex strip-absent region with an inner surface of the balloon body facing inwards to form a folded vane portion in which the convex strip-absent regions are laminated, and the folded vane portion is disposed overlaying the outer surface of the straight tubular part and covering a top of the convex strip.

7. The balloon according to claim 1, wherein:
the outer surface of the straight tubular part has a convex strip-present region where the convex strip is present and a convex strip-absent region where the convex strip is not present; and
in a contracted state of the balloon, the straight tubular part is folded back at the convex strip-absent region with an inner surface of the balloon body facing inwards to form a folded vane portion in which the convex strip-absent regions are laminated, and the folded vane portion is disposed overlaying the outer surface of the straight tubular part and not covering a top of the convex strip.

8. A balloon catheter comprising the balloon according to claim 1.

9. A balloon for a balloon catheter, having a longitudinal direction extending from a proximal side to a distal side and a radial direction perpendicular to the longitudinal direction, comprising:
a straight tubular part comprising a balloon body of a cylindrical shape and a multi-step convex strip which protrudes outwards in the radial direction on an outer surface of the balloon body;
a proximal tapered part located proximal to the straight tubular part;
a distal tapered part located distal to the straight tubular part; and
a drug layer provided on the outer surface of the straight tubular part including a lateral surface of the convex strip, wherein a crack is formed on a surface of the drug layer extending along a base of any one of steps of the multi-step convex strip.

10. The balloon according to claim 9, wherein the convex strip extends in the longitudinal direction of the balloon.

11. The balloon according to claim 9, wherein:
the outer surface of the straight tubular part has a convex strip-present region where the convex strip is present and a convex strip-absent region where the convex strip is not present; and
a thickness of the drug layer at the base of the convex strip, excluding a part where the crack is formed, is thicker than a thickness of the drug layer at a farthest point from the convex strip in the convex strip-absent region in a cross section perpendicular to the longitudinal direction of the straight tubular part.

12. The balloon according to claim 9, wherein a drug constituting the drug layer is crystalline.

13. The balloon according to claim 9, wherein the convex strip is made of resin, metal, or a combination thereof.

14. The balloon according to claim 9, wherein:
the outer surface of the straight tubular part has a convex strip-present region where the convex strip is present and a convex strip-absent region where the convex strip is not present; and
in a contracted state of the balloon, the straight tubular part is folded back at the convex strip-absent region with an inner surface of the balloon body facing inwards to form a folded vane portion in which the convex strip-absent regions are laminated, and the folded vane portion is disposed overlaying the outer surface of the straight tubular part and covering a top of the convex strip.

15. The balloon according to claim 9, wherein:
the outer surface of the straight tubular part has a convex strip-present region where the convex strip is present and a convex strip-absent region where the convex strip is not present; and
in a contracted state of the balloon, the straight tubular part is folded back at the convex strip-absent region with an inner surface of the balloon body facing inwards to form a folded vane portion in which the convex strip-absent regions are laminated, and the folded vane portion is disposed overlaying the outer surface of the straight tubular part and not covering a top of the convex strip.

16. A balloon catheter comprising the balloon according to claim 9.

17. A method for manufacturing a balloon catheter comprising:

preparing a balloon having a longitudinal direction extending from a proximal side to a distal side and a radial direction perpendicular to the longitudinal direction, wherein:

the balloon comprises a straight tubular part, a proximal tapered part located proximal to the straight tubular part, and a distal tapered part located distal to the straight tubular part; and the straight tubular part comprises a balloon body of a cylindrical shape and a convex strip which protrudes outwards in the radial direction on an outer surface of the balloon body;

applying a drug solution to the outer surface of the straight tubular part including a lateral surface of the convex strip, thereby forming a drug layer; and bending the convex strip relative to the outer surface of the balloon body after the forming the drug layer; wherein the bending the convex strip further comprises forming a crack on a surface of the drug layer extending along a base of the convex strip.

18. A method of claim 17, wherein the convex strip is a multi-step convex strip and the bending the multi-step convex strip further comprises forming the crack on the surface of the drug layer extending along a base of any one of steps of the multi-step convex strip.

* * * * *